(12) United States Patent
Lam et al.

(10) Patent No.: US 8,288,165 B2
(45) Date of Patent: Oct. 16, 2012

(54) MOLECULAR HETEROBIMETALLIC CHEMODOSIMETRIC SENSOR FOR THE DETECTION OF BIOGENIC AMINES

(75) Inventors: Hon-Wah Lam, Kowloon Tong (HK); Cheuk-Fai Chow, Ma Wan (HK)

(73) Assignee: City University of Hong Kong, Kowloon (HK)

( * ) Notice: Subject to any disclaimer, the term of this patent is extended or adjusted under 35 U.S.C. 154(b) by 0 days.

(21) Appl. No.: 12/797,763

(22) Filed: Jun. 10, 2010

(65) Prior Publication Data
US 2011/0306140 A1   Dec. 15, 2011

(51) Int. Cl.
*G01N 33/02* (2006.01)
*G01N 33/00* (2006.01)
*C07D 213/04* (2006.01)
*C07D 213/00* (2006.01)

(52) U.S. Cl. .......................... 436/164; 422/500; 422/50

(58) Field of Classification Search .................. 436/164; 422/50
See application file for complete search history.

(56) References Cited

U.S. PATENT DOCUMENTS

| | | | |
|---|---|---|---|
| 4,963,324 | A | 10/1990 | May |
| 7,332,343 | B2 | 2/2008 | Anslyn et al. |
| 2004/0072359 | A1 | 4/2004 | Southard |
| 2008/0299669 | A1 | 12/2008 | Lavigne et al. |

OTHER PUBLICATIONS

Koo et al., A Pair of Coordination Donor-Acceptor Ensembles for the Detection of Tartrate in Aqueous Media, Eur. J. Inorg. Chem., 2008, Wiley Inter Science, 1318-1325.*

Maynor MS et al. A food freshness sensor using the multistate response from analyte-induced aggregation of a cross-reaction polythiophene. Organic Letters 2007, 9, 3217-3220.

Nelson, TL et al. Multi-layered analyses using directed partitioning to identify and discriminate between biogenic amines. Analyst 2007, 132, 1024-1030.

Herrera, JM et al. Photophysical and structural properties of cyanoruthenate complexes of hexaazatriphenylene. Journal of the American Chemical Society 2007, 129, 11491-11504.

Herrera, JM et al. Structural and photophysical properties of coordination networks combining [Ru(Bpym)(CN)4]2-or [{Ru(CN)4}2(bpym)]4- anions (bpym=2,2'-bipyrimidine) with lanthanide(III) cations: sensitized near-infrared luminescence from Yb(III), Nd(III), and Er(III) following Ru-to-Lanthanide energy transfer. Inorganic Chemistry 2006, 45, 3895-3904.

Adams, H et al. New members of the [Ru(diimine)(CN)4]2- family: structural, electrochemical and photophysical properties. Dalton Transactions 2006, 39-50.

Gurskii, ME et al. The first preparation of (1S,5R)-(–)- and (1R,5S)-(+)-7-phenyl-3-borabicyclo[3.3.1]non-6-enes and their application for synthesis of chiral cyclohexene derivatives. Journal of Organometallic Chemistry (2005), 690 (11), 2840-2846.

Davies, GM et al. Structural and Photophysical Properties of Coordination Networks Combining [Ru(bipy)(CN)4]2-Anions and Lanthanide(III) Cations: Rates of Photoinduced Ru-to-Lanthanide Energy Transfer and Sensitized Near -Infrared Luminescence. Inorganic Chemistry (2005), 44(13), 4656-4665.

Miller, TA et al Photoinduced Ru-Yb energy transfer and sensitised near-IR luminescence in a coordination polymer containing co-crystallized [Ru(bipy)(CN)4]2- and Yb(III) units. Dalton Transactions (2004), (10), 1524-1526.

Koo, CK et al. A pair of coordination donor-acceptor ensembles for the detection of tartrate in aqueous media. Eur. J. Inorg. Chem. (2008), 1318-1325.

* cited by examiner

*Primary Examiner* — Christine T Mui
(74) *Attorney, Agent, or Firm* — Heslin Rothenberg Farley & Mesiti P.C.

(57) ABSTRACT

The invention relates to using heterobimetallic coordination polymers and their uses as chemodosimeters for sensing materials for the screening of specific biogenic amines.

8 Claims, 4 Drawing Sheets

MOLECULAR HETEROBIMETALLIC CHEMODOSIMETRIC SENSOR FOR THE DETECTION OF BIOGENIC AMINES

FIELD OF THE INVENTION

The invention relates to heterobimetallic coordination polymers and their uses as chemodosimeters for sensing materials for the screening of specific biogenic amines.

BACKGROUND OF THE INVENTION

Biogenic amines such as histamine, spermidine, putrescine, and trimethylamine are key compounds in living systems. They are low molecular weight organic bases in cells and are involved in many vital biological functions such as protein synthesis, regulation of cell proliferation, modulation of ion channels and change of gene expression. They are also important parameters to be monitored in clinical diagnostics and the food industry.

The detection of the neutral biogenic amines is of particular interest due to their importance in areas ranging from clinical diagnostics (as biomarkers of specific diseases) to quality control of food products. Biogenic amines are famous for their putrid and stinking smell. Some of them, such as histamine, spermidine and putrescine, are also key compounds in living systems and are involved in many vital biological functions, such as protein synthesis, regulation of cell proliferation and modulation of gene expression. They have also been the focus of medical and pharmaceutical research on the mechanisms of some of the biological disorders. For instance, high plasma levels of putrescine and spermidine have been associated with breast, colon and skin cancers. In food safety, wide ranges of biogenic amines are found as biomarkers for spoilage of fishes. Histamine, which has been identified as a neurotransmitter for anthropod photoreceptors, is the causative agent of scombroid food poisoning. Methods of detecting biogenic amines recently described in the literature have taken advantage of analytical instruments, molecular imprinting polymers and immunoassays.

Chemodosimeters are molecular devices that interact with their analytes and yield physically measurable signals in a ratiometric and irreversible fashion. In contrast to ordinary chemosensors which respond to the real-time concentration of their analytes, chemodosimeters respond to their analytes in a cumulative manner. These properties allow chemodosimeters to be especially suitable for food monitoring. Since the signals don't disappear (irreversible fashion), users/customers can recognize there is spoilage of food if contamination occurred at any time during the process (i.e., during food production, transportation or other processes).

SUMMARY OF THE INVENTION

Up to now, chromatographic determination has been the most widely adopted analytical approach for the detection of biogenic amines in food and in biomedical samples. It usually requires extraction of the amines from the sample followed by chemical derivatization before chromatographic analysis. Procedures involved are tedious and time-consuming. In fact, in most food safety inspections, rapid screening for the presence of biogenic amines is enough.

Thus, a chemodosimeter/chemosensor that can rapidly respond to the presence of biogenic amines and produces naked-eye detectable signals should be able to find a number of biomedical and food safety applications. A selective, low-cost and easy-to-use sensor for biogenic amines is highly desirable in many real world applications. However, reporting on this kind of sensors for biogenic amines is rather scarce. This invention relates to an indicator displacement chemodosimetric approach using heterobimetallic coordination polymers, enabling the development of a new generation of sensing materials for the screening of specific biogenic amines.

Classical molecular sensors are, in general, molecular assemblies of molecular recognition (receptor) units and signal transduction units where sensing responses are triggered by the receptor-analyte interaction. However, the requirement for the receptor-analyte binding events to trigger signal transduction has posed considerable constraints on their design and synthesis. This invention utilizes a new chemodosimetric scheme—the indicator displacement approach—that allows much greater flexibility to the molecular design of molecular sensors. One chemodosimeter used in this invention is a coordination polymer (denoted as $Ru_2Eu$-1) self-assembled from two transition metal coordination units, a ruthenium polypyridyl tetrakiscyano complex ($[Ru(^tBubpy)(CN)_4]^{2-}$, where $^tBubpy$=4,4'-tert-butylbipyridine) and an europium (III) ($Eu^{3+}$) metal centre, via a simple donor-acceptor adduct formation. The monomeric unit of this heterobimetallic coordination polymer can be represented by the molecular formula $\{[Eu^{III}(H_2O)_4]$—$[R^{II}(^tBubpy)(CN)_4]_2\}^-$. The molecular structure of this monomeric unit of the $Ru_2Eu$-1 coordination polymer is shown below:

$Ru_2Eu$-1

The hard Lewis acidic $Eu^{3+}$ metal centers in $Ru_2Eu$-1 act as electron acceptors and are coordinated to the lone-pairs of electrons on the N-terminal of the cyano ligands of the $[Ru(^tBubpy)(CN)_4]^{2-}$ units, which act as the electron donors. Such a donor-acceptor linkage is stable and intact even when $Ru_2Eu$-1 is dissolved in common polar solvents, such as ethanol, and has been confirmed by electrospray-mass spectrometry.

In one embodiment, the invention relates to a method of detecting the presence of a biogenic amine or ammonia in a sample comprising:
a. providing a complex of formula I $$M_A\text{-}C\equiv N\text{-}M_B \qquad (I)$$

wherein $M_A$ is a Ru(II) complex and $M_B$ is a lanthanide metal complex;
b. bringing the vapor of the sample into contact with said complex of formula I, whereby said biogenic amine or ammonia displaces the $M_A$-C≡N portion of the complex of formula I from the $M_B$ portion; and
c. detecting the presence of displaced $M_A$-C≡N by measuring a colorimetric response.

In one embodiment, the invention relates to a method for detecting a biogenic amine or ammonia in a food sample, comprising providing a complex of formula I $M_A$-C≡N-$M_B$ (I), wherein $M_A$ is a Ru(II) complex and $M_B$ is a lanthanide metal complex; exposing the complex to a food product; and detecting any change in color, said detected change being indicative of the presence of biogenic amine or ammonia in, on or in association with, the food product.

As an example, one could envision a packaged tray of meat or fish, wherein the tray (or the surrounding wrap) comprises an indicator strip containing the complex. If the meat or fish is not fresh, it will release vapors of biogenic amines and/or ammonia as it decays. When these vapors came into contact with the indicator strip containing the complex, they would react, causing a color change to alert the seller or the consumer that the meat is not fresh.

As another example, the complex could be part of a free-standing testing system to detect a food's freshness. In this case, for example, the complex could be in a hand-held indicator system wherein an operator would bring the system into contact with an area where biogenic amines and/or ammonia vapors may be present if food isn't fresh. Alternatively, the indicator system could be placed more permanently in a fresh meat rack.

In one embodiment, the invention relates to a process for preparing a complex of formula I (I)

comprising mixing a 2:1 ratio of $K_2[Ru(4,4'$-Di-tert-butyl-2, 2'-bipyridine)$CN)_4$] and $EuCl_3 \cdot 6H_2O$ together in a 1:1 mixture of water and alkanol.

In one embodiment, the invention relates to a dosimeter for detecting and/or measuring a biogenic amine or ammonia in, on or in association with a fluid which comprises a complex of the general formula $M_A$-C≡N-$M_B$ (I) and a support structure having a surface, the complex being attached to the support structure as a coating thereon, wherein said complex undergoes a detectable color change upon exposure to a biogenic amine or ammonia.

In one embodiment, the invention relates to a complex of formula Ic:

(Ic)

wherein $R^1$ in each instance is selected from $(C_1-C_6)$alkyl, phenyl, halogen and $(C_1-C_6)$alkoxy, and wherein $R^1$ may be located at any of the 3, 3', 4, 4', 5 and 5' positions on the bipyridine rings.

In one embodiment, the invention relates to a food container comprising the complex of formula I: $M_A$-C≡N-$M_B$ (I).

In one embodiment, the invention relates to a food container comprising the complex of formula II (II)

In one embodiment, the invention relates to a method of measuring the amount of a biogenic amine or ammonia in a sample comprising:
a. providing a complex of formula I
  i. $M_A$-C≡N-$M_B$ (I),
  ii. wherein $M_A$ is a Ru(II) complex and $M_B$ is a lanthanide metal complex;
b. bringing the vapor of the sample into contact with said complex of formula I, whereby said biogenic amine or ammonia displaces the $M_A$-C≡N portion of the complex of formula I from the $M_B$ portion; and
c. measuring the colorimetric response to determine the amount of displaced $M_A$-C≡N.

In one embodiment, the invention relates to the detection and/or measurement of vapor phase biogenic amines and ammonia. The sample to be tested may contain other interfering molecules that may decrease the selectivity and/or sensitivity of the heterobimetallic complex for these amines and ammonia. However, our dosimeters show specific detection of the vapor form of the biogenic amines and ammonia because (i) our dosimeters are very selective and sensitive to lone pair electrons of amines and ammonia functionalities; and (ii) the biogenic amines and ammonia having a modest vapor pressure can already differentiate themselves from interfering molecules, which are less likely to be in the vapor phase.

DETAILED DESCRIPTION OF THE INVENTION

In one embodiment, the invention relates to a method of detecting the presence of a biogenic amine or ammonia in a sample. This may be done by:

a. providing a complex of formula I (I), wherein $M_A$ is a Ru(II) complex and $M_B$ is a lanthanide metal complex;

b. bringing the vapor of the sample into contact with said complex of formula I, whereby said biogenic amine or ammonia displaces the $M_A$-C≡N portion of the complex of formula I from the $M_B$ portion; and c. detecting the presence of displaced $M_A$-C≡N by measuring a colorimetric response.

In one embodiment, the invention relates to a method for detecting and/or measuring a biogenic amine or ammonia in a food sample. This may be done by a. providing a complex of formula I $M_A$-C≡N-$M_B$ (I), wherein $M_A$ is a Ru(II) complex and $M_B$ is a lanthanide metal complex;

b. exposing the complex to a food product; and c. detecting any change in color, said detected change being indicative of the presence of biogenic amine or ammonia in, on or in association with, the food product.

In some embodiments, the invention relates to a process for preparing a complex of formula I:

This process comprises mixing a 2:1 ratio of $K_2$[Ru(4,4'-Di-tert-butyl-2,2'-bipyridine)$CN)_4$] and $EuCl_3.6H_2O$ together in a 1:1 mixture of water and alkanol.

In some embodiments, the invention relates to a sensor for detecting the presence of a biogenic amine or ammonia in, on or in association with a fluid which comprises a complex of the general formula $M_A$-C≡N-$M_B$ (I) and a support structure having a surface, the complex being attached to the support structure as a coating thereon, wherein said complex undergoes a detectable color change upon exposure to a biogenic amine or ammonia. It is to be understood that the biogenic amine or ammonia to be detected may be in the vapor phase. In some embodiments, the structure comprises a plastic sheet, film or tray food packaging. In other embodiments, the structure comprises a gas permeable film or membrane.

In some embodiments, the invention relates to a food container comprising the complex of formula I: $M_A$-C≡N-$M_B$ (I).

In some embodiments, the invention relates to a food container comprising the complex of formula II In some embodiments, the invention relates to a method of measuring the amount of a biogenic amine or ammonia in a sample. This may be accomplished by:

a. providing a complex of formula I

(I), wherein $M_A$ is a Ru(II) complex and $M_B$ is a lanthanide metal complex;

b. bringing the vapor of the sample into contact with said complex of formula I, whereby said biogenic amine or ammonia displaces the $M_A$-C≡N portion of the complex of formula I from the $M_B$ portion; and c. measuring the colorimetric response to determine the amount of displaced $M_A$-C≡N.

In some embodiments, the invention relates to a complex of formula Ic:

In some embodiments, $R^1$ is $(C_1-C_6)$alkyl. For instance, $R^1$ may be t-butyl. In other embodiments, $R^1$ is phenyl. In still other embodiments, $R^1$ is halogen. For instance, $R^1$ may be fluorine, bromine or chlorine. In yet other embodiments, $R^1$ is $(C_1-C_6)$alkoxy. As an example, $R^1$ may be methoxy or ethoxy. To be perfectly clear, $R^1$ in each instance may be selected from any of the above options. For instance, in one embodiment, $R^1$ may be t-butyl on one pyridine group, methyl on another pyridine, fluorine on a third pyridine and methyl on the fourth pyridine. In another embodiment, $R^1$ may be t-butyl on all four pyridines. $R^1$ may be located at any of the 3, 3', 4, 4', 5 and 5' positions on the bipyridine rings.

In some embodiments of the invention, the complex is of formula Ia:

(Ia).

In other embodiments of the invention, the complex is of formula Ic:

(Ic)

In some embodiments, R¹ in each instance is t-butyl, such as is found in formula II:

(II)

In some embodiments of the invention, the complex may be of stereochemistry

In some embodiments of the invention, the sample comprises ammonia. In other embodiments, the sample comprises an amine with aliphatic amino functionality. In some embodiments, the amine is histamine. In other embodiments, the amine is spermidine. In still other embodiments, the amine is putrescine. In yet other embodiments, the amine is cadaverine. In some embodiments, the sample comprises an amine with aromatic amino functionality. In some embodiments, the amine is aniline.

In some embodiments of the invention, the complex is in a suitable solvent. A "suitable solvent" is one in which the complex is sufficiently soluble to allow the reaction between ammonia or a biogenic amine and the complex to take place. Illustrative suitable solvents include alkanols and other solvents, such as dimethyl sulphoxide and dimethylformamide.

In some embodiments of the invention, the vapor of the sample is brought into contact with the complex. This technique will be especially desirable when testing for biogenic amines or ammonia as it relates to food products, as it will not be necessary for the chemical complex to come into direct contact with the food itself.

In some embodiments of the invention, a colorimetric response is detected. In some embodiments, the colorimetric response is ultraviolet light or emission. In other embodiments, the colorimetric response is visible light or emission.

DEFINITIONS

Throughout this specification the terms and substituents retain their definitions.

Alkyl is intended to include linear, branched, or cyclic hydrocarbon structures and combinations thereof. A combination would be, for example, cyclopropylmethyl. Hydrocarbon refers to any substituent comprised of hydrogen and carbon as the only elemental constituents. Lower alkyl refers to alkyl groups of from 1 to 6 carbon atoms. Examples of lower alkyl groups include methyl, ethyl, propyl, isopropyl, cyclopropyl, butyl, s- and t-butyl, cyclobutyl and the like. Preferred alkyl groups are those of $C_{20}$ or below. Cycloalkyl is a subset of alkyl and includes cyclic hydrocarbon groups of from 3 to 8 or more carbon atoms. Examples of cycloalkyl groups include c-propyl, c-butyl, c-pentyl, norbornyl and the like.

Substituents R″ are generally defined when introduced and retain that definition throughout the specification and in all independent claims.

A "sample" refers to a solution that may contain one or more biogenic amines. The sample may be the material of interest or it may be derived from a material of interest by an extraction process. Commonly, because biogenic amines have a modest vapor pressure, the extraction process may involve a vapor phase. If the analysis involves a vapor phase, the vapor phase may be brought into a separate solution to enhance analysis, for instance, in a buffered solution. For example, if the sample of interest is a food product, which is itself a solid, a liquid or a mixture of the two, the sample could be the liquid portion of the product or it could be the vapor in the head space above the product. Further, the sample could be obtained by sparging the sample with a carrier gas and then measuring the biogenic amine in the carrier gas. In both instances in which the biogenic amine is in the vapor phase, it will be brought into contact with a separate solution in which the compounds of the invention are dissolved or suspended.

Aliphatic amino functionality refers to an amine that is attached directly to a non-aromatic moiety. For example, spermidine possesses aliphatic amino functionality, while aniline does not:

Aromatic amino functionality, on the other hand, refers to an amine that is attached directly to an aromatic moiety. In this case, aniline possesses aromatic amino functionality, while spermidine does not.

The term "colorimetric response" is meant to include any qualitative or quantitative response measurable by, for instance, visual or spectroscopic methods. This could include luminescence, phosphorescence, fluorescence, visible light color changes or UV light measurements.

"Contact" refers to the physical contact of at least one substance to another substance. For instance, a vapor of a sample, such as a biogenic amine or a substance containing a biogenic amine, is considered to be in contact with a heterobimetallic complex of the invention if the biogenic amine is able to react with the heterobimetallic complex.

"Fluid" is meant to represent liquid or gas (vapor).

ABBREVIATIONS

A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations", is incorporated herein by reference. The following abbreviations and terms have the indicated meanings throughout:

| | |
|---|---|
| $^t$Bubpy = | 4,4'-tert-butylbipyridine |
| Et = | ethyl |
| EtOH = | ethanol |
| MLCT = | metal-to-ligand charge transfer |
| Me = | methyl |
| ppb = | parts per billion |
| ppm = | parts per million |

EXPERIMENTAL SECTION

Materials and Reagents 4,4'-Di-tert-butyl-2,2'-bipyridine ($^t$Bubpy), potassium cyanide, $RuCl_3.3H_2O$, $EuCl_3.6H_2O$ aniline, histamine, putrescine, spermidine and anhydrous gaseous $NH_3$ (99.99%) were obtained from Aldrich. Gaseous $H_2S$ (99.5%) and CO (99.95%) were obtained from Hong Kong Special Gas Company. Gaseous $CH_4$ (99.95%), $H_2$ (99.995%) and $N_2$ (99.995%) were purchased from Hong Kong Oxygen Company. $K_2[Ru(^tBubpy)(CN)_4]$ was synthesized according to literature method. (M. Kato, S. Yamauchi, N. Hirota, *J. Phys. Chem.* 1989, 93, 3422.) All solvents used were of analytical grade.

Physical Measurements and Instrumentation

Infrared spectra in the range 500-4000 $cm^{-1}$ in KBr plates were recorded on a Perkin Elmer Model FTIR-1600 spectrometer. UV-vis spectra were measured on a Hewlett Packard 8452A ultraviolet visible diode array spectrophotometer. Emission spectra were recorded using a Horiba FluoroMax-3 spectrofluorimetric with 5 nm slit width and 0.5 s integration time. $^1$H-NMR spectra were recorded using a Varian YH300 300 MHz NMR spectrometer. Electrospray mass spectra (ESI-MS) were measured by a PE SCIEX API 365 LC/MS/MS system. Elementary analyses were performed on a Vario EL elementary analyzer.

$K\{[Eu(H_2O)_4]-[Ru(^tBubpy)(CN)_4]_2\}.8H_2O(Ru_2Eu-1)$

A mixture of $K_2[Ru(^tBubpy)(CN)_4]$ (0.110 g, 0.2 mmol) and $EuCl_3.6H_2O$ (0.037 g, 0.1 mmol) was stirred in 5 ml of a water/methanol mixture (1:1) at room temperature for 30 min. and was allowed to stand overnight. Yellow crystalline plates were obtained by slow evaporation of solvent. Yield: 0.084 g (69%). IR (KBr): $v_{C\equiv N}$=2061, 2105 $cm^{-1}$. ESI-MS (−ve mode): m/z 1099 $\{[Eu]-[Ru(^tBubpy)(CN)_4]_2\}^-$. Anal. Calcd. for $C_{44}EuH_{56}KN_{12}O_4Ru_2.7H_2O$: C, 39.55; H, 5.28; N, 12.58. Found: C, 39.54; H, 5.24; N, 12.58.

Crystal Structure Determination

Yellow single plated crystals of complex $Ru_2Eu-1$ were grown by slow evaporation of its corresponding aqueous methanol solution in open atmosphere. Geometric and intensity data for the complex was collected on a Bruker SMART 1K CCD area detector with graphite monochromated Mo—Kα radiation (λ=0.71073 Å). Crystal of the complex used for data collection was mounted in glass capillaries to prevent rapid solvent loss. The collected frame was processed with the software CrystalClear (Rigaku). The data was corrected for Lorentz and polarization effects. A correction for secondary extinction was applied to the collected reflections. The structure of the complex was solved by direct methods (SHELX97) in conjunction with standard difference Fourier techniques and subsequently refined by full-matrix least-square were analyzed on $F^2$. Non-hydrogen atoms were refined anisotropic displacement parameters except for the atoms of some of the free water molecules where these atoms were refined isotropically. The hydrogen atoms were generated in their idealized positions and allowed to ride on the respective carbon atoms.

Characterization $Ru_2Eu-1$ has been fully characterized by X-ray crystallography, electrospray-mass spectrometry and elemental analysis.

The electron donor $[Ru(^tBubpy)(CN)_4]^{2-}$ is brightly luminescent under photo-excitation in the visible range (λ=400-500 nm). In an ethanol solution at room temperature, it possesses a UV-vis absorption peak at ca. 435 nm and a broad emission peak at ca. 654 nm. Without wishing to be restricted to this proposed mechanism, Applicants believe the UV-vis absorption is due to the Ru(dπ)→$^t$Bubpy(π*) MLCT transition, and the orange-red color luminescence is attributable to the radiational phosphorescent relaxation of the $^3$MLCT excited state. Upon coordination with the $Eu^{3+}$ electron acceptors and the formation of the $Ru_2Eu-1$ coordination complex, the UV-vis absorption band of $[Ru(^tBubpy)(CN)_4]^{2-}$ is blue-shifted to 417 nm and the photoluminescence at 650 nm is blue-shifted to 644 nm with a drastic reduction in luminescent intensity. It is believed that the blue-shift of the UV-vis absorption and emission peaks is due to the increase in effective nuclear charge of the Ru(II) metal centre as the σ-donating ability of the cyano ligands is weakened upon coordination with electron acceptors. It is also believed that the decrease of the $^3$MLCT emission intensity is attributable to the concomitant increase in energy of the $^3$MLCT state and the decrease in energy of the non-emissive d-d* state of $[Ru(^tBubpy)(CN)_4]^{2-}$, which results in the quenching of the $^3$MLCT luminescence.

Figure 1:
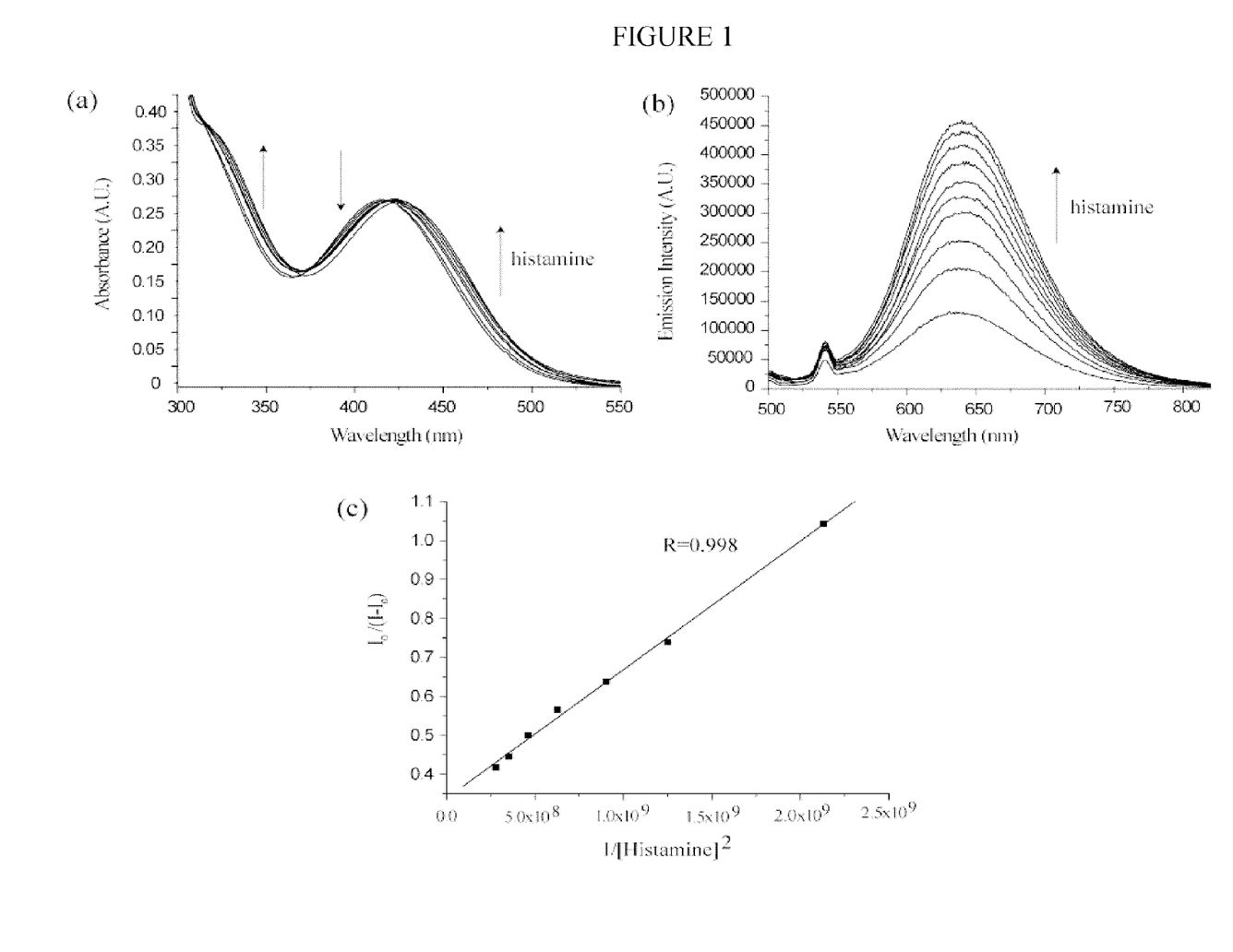
FIG. 1: Spectroscopic and spectrofluorometric responses of $Ru_2Eu$-1 to histamine.

When ammonia ($NH_3$) gas or vapor of organic amines is bubbled into an ethanol solution of $Ru_2Eu-1$, the UV-vis absorption and the characteristic luminescent properties of $[Ru(^tBubpy)(CN)_4]^{2-}$ is resumed in the solution. FIG. 1 shows the typical spectroscopic and spectrofluometric changes of $Ru_2Eu-1$ upon the addition of histamine as a model organic amine. FIGS. 1(*a*) and 1(*b*) show the UV-vis spectroscopic changes and spectrofluorimetric changes of the titration of $Ru_2Eu-1$ (3.33×10$^{-5}$ M) with histamine (0 to 6.67×10$^{-5}$ M). FIG. 1(*c*) illustrates the fitting of the spectrofluorometric data into a 1:2 ($Ru_2Eu-1$: histamine) Benesi-Hildebrand binding model, revealing a binding constant of log K=4.51±0.03 $M^{-1}$. All titrations were carried out in EtOH at 298 K with excitation at 466 nm.

Without wishing to be restricted to this proposed mechanism, Applicants believe that these results are due to the histamine displacing the ruthenium species from the europium complex to free the $[Ru(^tBubpy)(CN)_4]^{2-}$ units, which act as luminescent indicators to reveal the presence of ammonia and/or organic amines. The observation of $\{K+[Ru(^tBubpy)(CN)_4]\}^-$ (m/z 513 $[M+K]^-$) and $[Eu(histamine)_2(H_2O)_2(OH)_2]^+$ (m/z 445 $[M-2H^+]^+$) in the electrospray ionization mass spectrometry (ESI-MS) of $Ru_2Eu$-1— biogenic amine mixtures suggests that this mechanism is correct.

Figure 2:
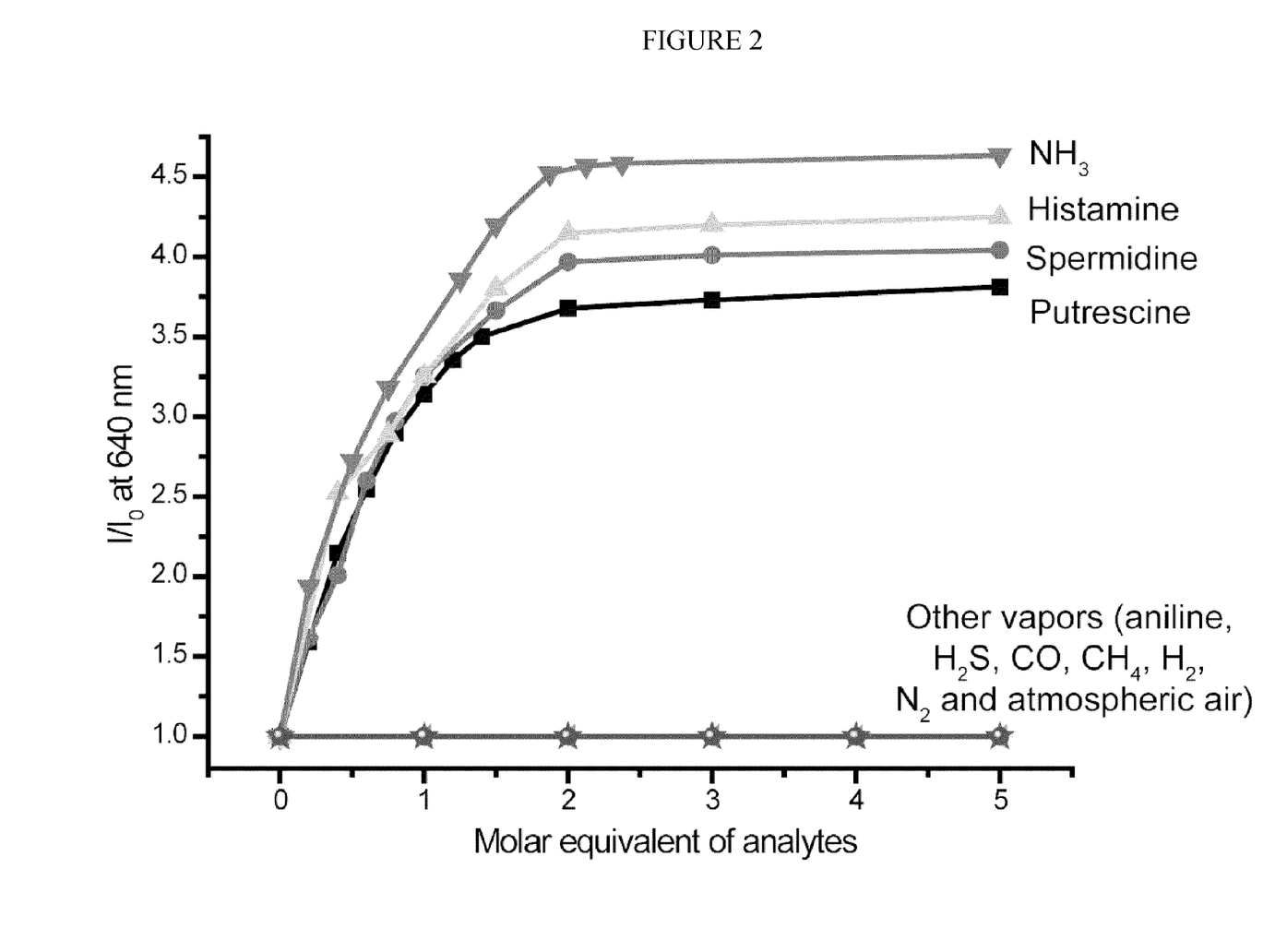
FIG. 2: Summaries of spectrofluorometric titration of $Ru_2Eu$-1 to various analytes.

FIG. 2 summarizes the spectrofluorimetric titration ($I/I_0$ at 640 nm) of $Ru_2Eu$-1 ($1.0\times10^{-4}$ M) with common volatile analytes including biogenic amines (histamine, putrescine, spermidine and aniline) and other common gases, such as ammonia ($NH_3$), hydrogen sulfide ($H_2S$), carbon monoxide (CO), methane ($CH_4$), dihydrogen ($H_2$), dinitrogen ($N_2$), atmospheric air and aniline ($NH_2$—$C_6H_5$). These analytes were monitored as a function of their concentrations. All titrations were carried out in ethanol at 298 K with excitation at 466 nm. Among all the analytes, only those with aliphatic amino functionality (histamine, putrescine, spermidine and ammonia) are able to induce the spectrofluorometric responses. Aromatic amino functionality and other common moieties are not able to induce any observable spectrofluorometric changes. In the case of spermidine, $Ru_2Eu$-1 can produce a luminescent response at a level of 10 ppb (10 ng-amine $ml^{-1}$), which is among the highest detection sensitivity for biogenic amines in the literature.

Table 1 summarizes the formation constant, log K, and the detection limit of $Ru_2Eu$-1 for histamine, putrescine, spermidine, aniline, ammonia and other common gases ($H_2S$, CO, $CH_4$, $H_2$, $N_2$ and atmospheric air) in EtOH at 298K:

TABLE 1

Summaries of the formation constants (log K) and detection limits of $Ru_2Eu$-1 with histamine, putrescine, spermidine, aniline, ammonia, $H_2S$, CO, $CH_4$, $H_2$, $N_2$ and atmospheric air in EtOH at 298 K.

|  | log K | Detection limits |
|---|---|---|
| Putrescine[a] | 4.86 ± 0.02 | 27 ppb |
| Spermidine[a] | 4.72 ± 0.01 | 10 ppb |
| Histamine[a] | 4.51 ± 0.03 | 30 ppb |
| $NH_3$[a] | 4.58 ± 0.03 | 79 ppb |
| Aniline[a] | 1.61 ± 0.08 | 89 ppm |
| Other common vapors ($H_2S$, CO, $CH_4$, $H_2$, $N_2$ and atmospheric air) | —[b] | —[c] |

[a] Formation constants (log K) of $Ru_2Eu$-1 towards various analytes were determined by plotting the best fitted $I_0/(I-I_0)$ vs. $1/[analyte]^2$ with 1:2 Benesi-Hildebrand equation;
[b] Formation constants (log K) were too small to be detected.
[c] Detection limits were unable to calculated.

Figure 3:
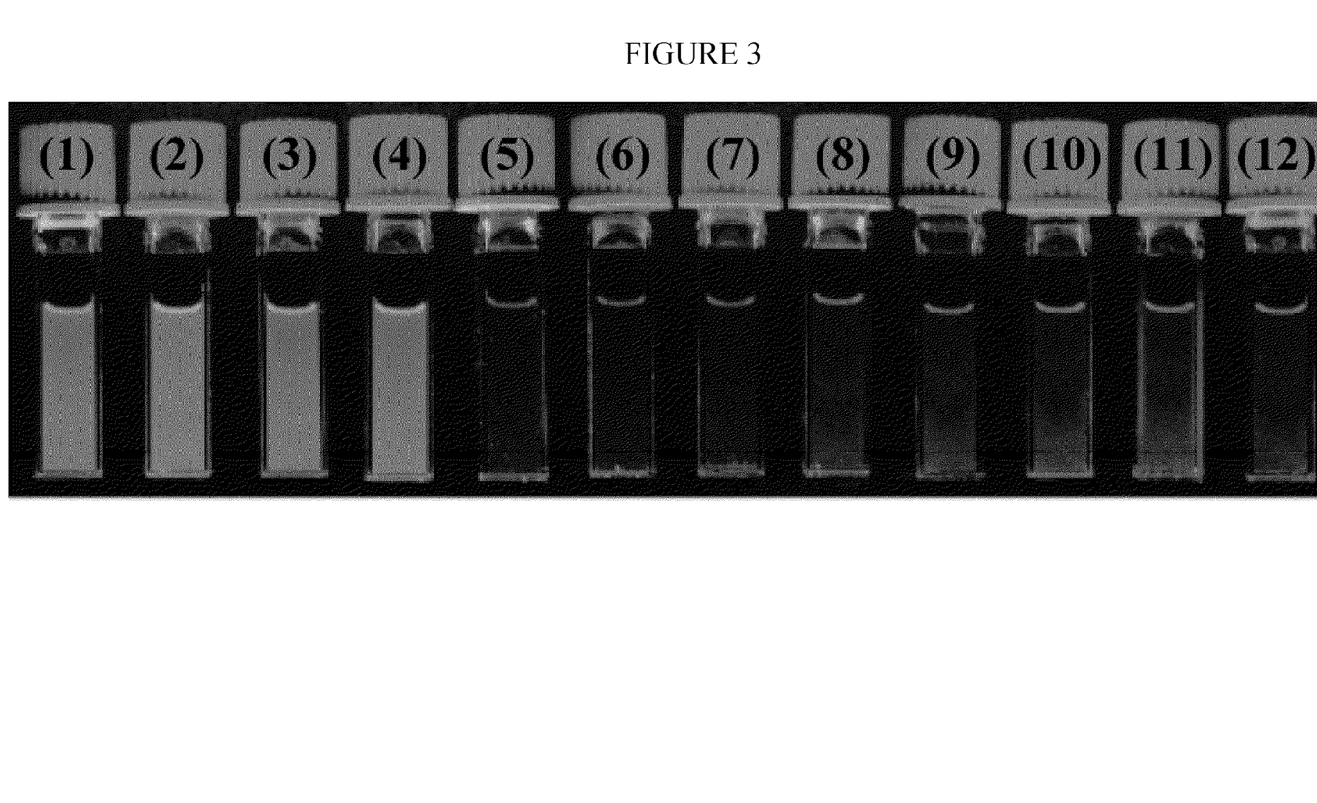
FIG. 3: Photographs of the luminometric responses of the $Ru_2Eu$-1 in EtOH at 298 K.

Luminescent responses of $Ru_2Eu$-1 can actually be detected with the naked eye. FIG. 3 shows the photographs of the luminometric responses of the $Ru_2Eu$-1 ($1.0\times10^{-4}$ M) in EtOH at 298 K and 1 atmospheric pressure. 3 ml of each gaseous sample of $NH_3$, $H_2S$, CO, $CH_4$, $H_2$, $N_2$, atmospheric air and vapors of histamine, aniline, putrescine and spermidine (over the headspace of their neat compounds) was purged into the headspace of ethanolic solutions of $Ru_2Eu$-1. (1) $Ru_2Eu$-1+histamine; (2) $Ru_2Eu$-1+putrescine; (3) $Ru_2Eu$-1+spermidine; (4) $Ru_2Eu$-1+$NH_3$; (5) $Ru_2Eu$-1 only; (6) $Ru_2Eu$-1+aniline; (7-12) $Ru_2Eu$-1+$H_2S$, CO, $N_2$, $CH_4$, $H_2$ and air respectively. Excitation $\lambda_{ex}$=365 nm.

Figure 4:
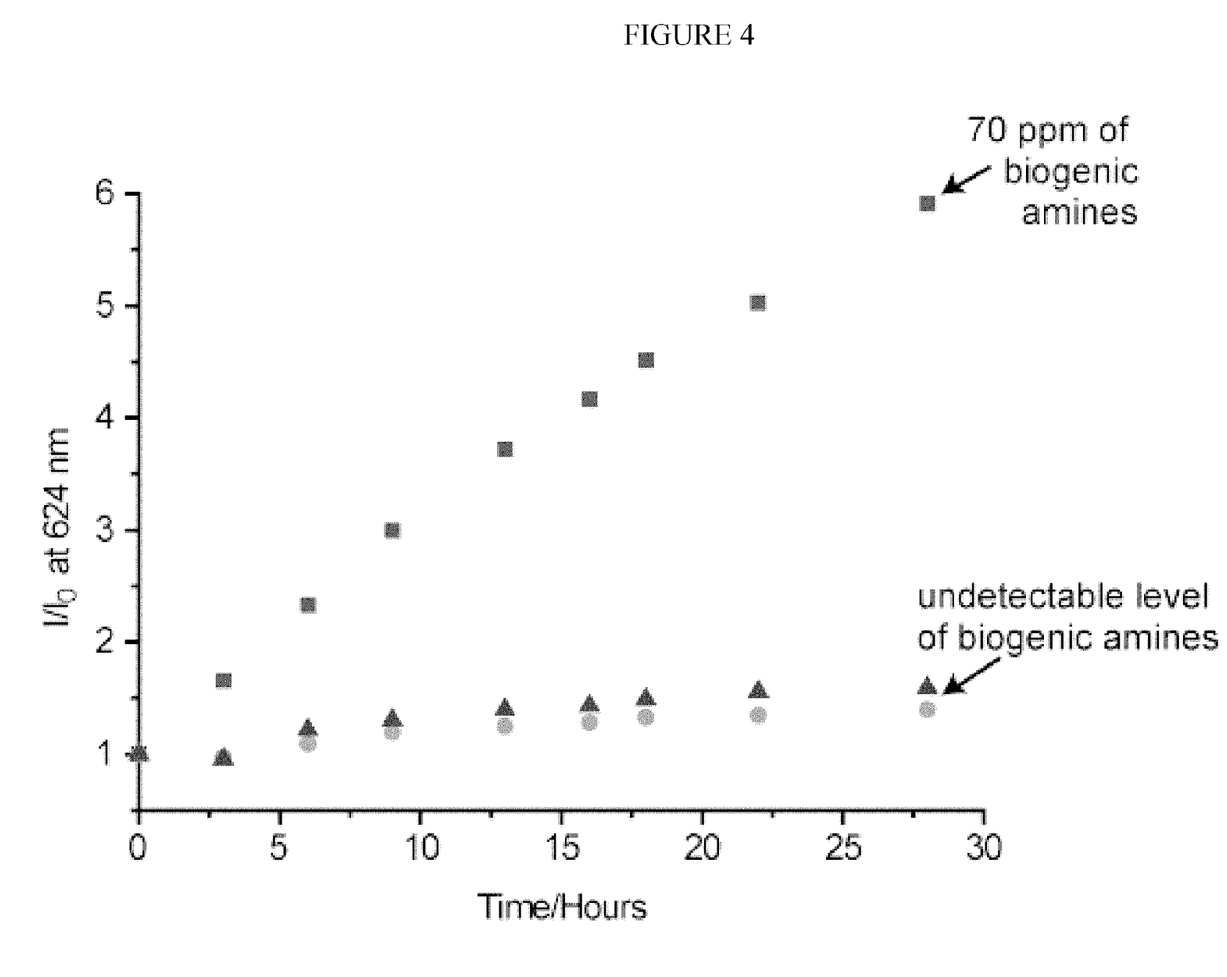
FIG. 4: Time trends of spectrofluorometric responses of $Ru_2Eu$-1 to the headspace vapor from homogenized fish meat.

For the final verification of the chemodosimetric detection of biogenic amines by $Ru_2Eu$-1, the chemosensor was used to examine the freshness of Atlantic mackerel (*Scomber scombrus*). 60.0 g of fresh Atlantic mackerel loin was homogenized and kept sealed in three separated 50 ml glass containers. These fish meat samples were subjected to three different storage conditions: room temperature, frozen temperature (0° C.) and room temperature with 60 g of a chemical preservative (sodium nitrite, $NaNO_2$). FIG. 4 summarizes the spectrofluorimetric responses of $Ru_2Eu$-1 ($3.33\times10^{-5}$ M in ethanol) to 20 ml of vapor sampled from the headspace of these enclosed containers. The time trends of spectrofluorometric responses ($H_0$ at 624 nm) of $Ru_2Eu$-1 ($3.33\times10^{-5}$ M in EtOH) to the headspace vapour (20 ml) from 20.0 g of homogenized Atlantic Mackerel (*Scomber scombrus*) fish meat stored under: (■) room temperature conditions; (●) frozen (0° C.) temperature conditions; and (▲) room temperature conditions in the presence of 60 g of sodium nitrite as preservative are shown. All titrations were carried out in ethanol at 298 K with excitation at 466 nm. Levels of biogenic amines (putrescine, cadaverine, histamine and spermidine) in the fish meat samples were determined by GC/MS analyses.

Among all the storage conditions, only the fish sample storing at room temperature showed an enhancement of spectrofluorometric responses with storage time. GC-MS analysis showed that, after 30 hours of storing at room temperature, extracts from the fish meat samples contained putrescine, cadaverine, histamine and spermidine, which were shown as characteristic peaks at retention times 10.8, 11.4, 11.8, 15.5 minutes, respectively. Levels of these four biogenic amines were estimated to be ≧70 ppm. (It is worth noting that 50 ppm of histamine is classified as the borderline of freshness of fish.) At frozen temperature and in the presence of a chemical preservative, no biogenic amine was detected by GC-MS after 30 hours of storage.

The invention claimed is:

1. A sensor for detecting and/or measuring a biogenic amine or ammonia in, on or in association with a fluid which comprises a complex of formula (I)

$$M_A\text{-}C\equiv N\text{-}M_B \tag{I}$$

and a support structure having a surface, the complex being attached to the support structure as a coating thereon, wherein said complex undergoes a detectable color change upon exposure to a biogenic amine or ammonia, and wherein $M_A$ is a Ru(II) complex and $M_B$ is a lanthanide metal complex.

2. A sensor of claim 1 wherein the support structure comprises a plastic sheet, film or tray food packaging or a gas permeable film or membrane.

3. A sensor of claim 1 wherein said complex is of formula II

4. A sensor of claim 1 wherein the fluid contains ammonia or an amine with aliphatic or aromatic amino functionality.

5. A sensor of claim 4 wherein the amine is selected from histamine, spermidine, putrescine, cadaverine and aniline.

6. A sensor of claim 1 wherein the complex is in a suitable solvent.

7. A sensor of claim 1 wherein the a vapor of the fluid is brought into contact with the complex.

8. A sensor of claim 1 wherein the colorimetric response detectable color change is ultraviolet or visible light or emission.

* * * * *

UNITED STATES PATENT AND TRADEMARK OFFICE
CERTIFICATE OF CORRECTION

PATENT NO. : 8,288,165 B2
APPLICATION NO. : 12/797763
DATED : October 16, 2012
INVENTOR(S) : Lam et al.

It is certified that error appears in the above-identified patent and that said Letters Patent is hereby corrected as shown below:

Column 12, Line 63: Claim 8, Delete "colorimetric response"

Signed and Sealed this
Fourth Day of December, 2012

David J. Kappos
*Director of the United States Patent and Trademark Office*